(12) United States Patent
Govindaswamy

(10) Patent No.: US 6,207,452 B1
(45) Date of Patent: Mar. 27, 2001

(54) ANTIBODY OF THE ANTI-PROLIFERATION DOMAIN OF HUMAN BCL-2

(75) Inventor: Chinnadurai Govindaswamy, St. Louis, MO (US)

(73) Assignee: St. Louis University Health Sciences Center, St. Louis, MO (US)

( * ) Notice: Subject to any disclaimer, the term of this patent is extended or adjusted under 35 U.S.C. 154(b) by 0 days.

(21) Appl. No.: 09/274,647

(22) Filed: Mar. 23, 1999

Related U.S. Application Data

(62) Division of application No. 09/079,186, filed on May 15, 1998, now Pat. No. 5,952,179, which is a division of application No. 08/652,245, filed on May 23, 1996, now Pat. No. 5,821,082.

(51) Int. Cl.[7] .............................. C07K 16/30; C12N 5/12
(52) U.S. Cl. .................. 435/330; 530/387.9; 530/388.1; 530/388.8; 530/389.7; 530/387.7; 435/331; 435/346
(58) Field of Search .............................. 530/387.7, 387.9, 530/388.1, 388.8, 389.7; 424/185.1; 435/330, 331, 346

(56) References Cited

U.S. PATENT DOCUMENTS

| | | | |
|---|---|---|---|
| 5,459,251 | 10/1995 | Tsujimoto et al. | 536/23.5 |
| 5,539,085 | 7/1996 | Bischoff et al. | 530/350 |
| 5,691,179 | 11/1997 | Korsmeyer | 435/240.1 |
| 5,700,638 | 12/1997 | Korsmeyer | 435/6 |
| 5,705,342 | 1/1998 | Bischoff et al. | 435/6 |

FOREIGN PATENT DOCUMENTS

WO95/05750  3/1995  (WO) .

OTHER PUBLICATIONS

Hunter et al., A peptide sequence from Bax that converts Bcl–2 into an activator of apoptosis, J. Biol. Chem., 271(15):8521–8524, Apr. 1996.*

Z. Songyang et al., "SH2 Domains Recognize Specific Phosphopeptide Sequences," Cell, 72:767–778 (1993).

J. Saras et al., "Characterization of the Interactions between PDZ Domains of the Protein–tyrosine Phosphatase PTPL1 and the Carboxyl–terminal Tail of Fas," J. Bio. Chem., 272:20979–20981 (1997).

Tanaka et al., "Structure–function analysis of the Bcl–2 oncogene protein," J. Biol. Chem., 268(15):10920–10926 (1993).

Theodorakis et al., "Unmasking of a proliferation–restraining activity of the anti–apoptosis protein EBV BHRF1," Oncogene, 12:1707–1713 (1996).

Uhlmann et al., "Deletion of a nonconserved region of Bcl–2 confers a novel gain of function: suppression of apoptosis with concomitant cell proliferation," Cancer Res., 5:2506–2509 (1996).

* cited by examiner

Primary Examiner—Elizabeth Kemmerer
Assistant Examiner—Claire M. Kaufman
(74) Attorney, Agent, or Firm—Sughrue, Mion, Zinn, Macpeak & Seas, PLLC

(57) ABSTRACT

A domain of Bcl-2 that suppresses apoptosis by allowing cell survival permits cell proliferation when mutated. The wild type domain includes amino acid residues 51 to 97 (SEQ ID NO:13) of Bcl-2. Peptides including the domain and nucleotides encoding the domain are useful in molecular screening of human tumors for the presence of mutations that allow proliferation of cells that were otherwise marked for apoptosis. The peptides are also useful to screen for proteins that play a role in the modulation of cellular proliferation.

6 Claims, 6 Drawing Sheets

ANTIBODY OF THE ANTI-PROLIFERATION DOMAIN OF HUMAN BCL-2

This application is a divisional of U.S. application Ser. No. 09/079,186, filed May 15, 1998, now U.S. Pat. No. 5,952,179, which is a divisional of U.S. application Ser. No. 08/652,245, filed May 23, 1996, now U.S. Pat. No. 5,821,082.

This invention was made with government support under grants CA-33616 and CA-31719 from the National Cancer Institute. The government has certain rights in the invention.

FIELD OF THE INVENTION

The present invention relates generally to the field of cell physiology, and more particularly to tumorigenesis and to apoptosis, i.e. programmed cell death. The novel peptides and nucleotides of the invention are useful in molecular screening of human tumors for the presence of mutations that allow the proliferation of cells that were otherwise marked for apoptosis. The novel peptides and nucleotides are also useful to screen for proteins that play a role in the modulation of cellular proliferation.

BACKGROUND OF THE INVENTION

The bcl-2 gene was discovered as typically involved in the t(14;18) chromosomal translocations observed in human follicular lymphoma (1–3). This chromosomal rearrangement results in deregulated high-level expression of the bcl-2 gene. In addition, Bcl-2 is also expressed at elevated levels in a variety of other tumors (4–6). The Bcl-2 protein suppresses apoptosis induced by a multitude of stimuli (7,8). Suppression of apoptosis by Bcl-2, while allowing cell survival, is characterized by growth arrest associated with Bcl-2 activity (40). Although bcl-2 was discovered as a candidate oncogene, conventional transformation assays indicate that it does not possess dominant oncogenic activity (9). It is therefore believed that unlike other oncogenes, bcl-2 contributes to oncogenesis primarily by extending cell viability, thereby perturbing the homeostatic mechanisms that control cell number and by providing an environment for other genetic changes (10).

In spite of a lack of detectable autonomous transforming activity, bcl-2 has been shown to synergize with c-myc in the generation of malignant cells (11). Since constitutive expression of c-myc induces apoptosis under certain conditions (12–14) that can be suppressed by Bcl-2 (14–16), it appears that the c-myc-cooperating oncogenic activity of bcl-2 may be related to its anti-apoptosis activity. In addition, Bcl-2 can also efficiently suppress apoptosis induced by tumor suppressor proteins such as p53 (17–21). This suggests that Bcl-2 may contribute to oncogenesis by suppressing apoptosis induced by oncogenes and tumor suppressor genes.

Although mutations within the Bcl-2 protein that permit proliferation of cells that would otherwise undergo total apoptosis could play a more direct role (as opposed to deregulated expression) in oncogenesis, thus far no such mutants have been identified in naturally arising tumors or under experimental conditions.

SUMMARY OF THE INVENTION

The present inventor here describes the identification and characterization of a hitherto unrecognized domain within human Bcl-2, which the inventor has designated the "anti-proliferation (AP) domain", that is required for the proliferation-restraining activity of Bcl-2. Mutants in this domain of Bcl-2 are described that retain the ability to suppress apoptosis induced by the p53 tumor suppressor protein and Myc onco-protein, while allowing concomitant cell proliferation.

More specifically, the present inventor has identified a deletion mutant of Bcl-2 that has a novel activity. The deletion mutant, designated Bcl2Δ51-85, not only suppresses apoptosis induced by the tumor suppressor protein p53 and the Myc onco-protein, but unlike wt Bcl-2, permits continued cell proliferation. These results may have important implications for oncogenesis involving Bcl-2. Unlike other oncogenes, the bcl-2 proto-oncogene promotes cell survival without significant cell proliferation. These results suggest that certain mutations can inactivate a proliferation-restraining activity. Further, the observed effect against oncogene/anti-oncogene-induced apoptosis may potentially prove to be of considerable significance in oncogenic events involving Bcl-2. Such inactivating mutations within the non-conserved region of Bcl-2 may enhance tumorigenesis by antagonizing the apoptotic activities of p53 and Myc as well as by permitting continued cell proliferation.

The molecular basis for the loss of proliferation-restraining activity in the Bcl-2 mutant has been partially elucidated as described in Example 3. The results suggest that the loss of activity does not correlate with the ability of Bcl-2 to interact with several proteins. However, the interaction between the Bcl-2 mutant and the death-promoting protein Bax appears to be enhanced compared to the interaction of Bax with wild type Bcl-2. It is not clear whether this enhancement is due to an increased affinity of the Bcl-2 mutant for Bax or increased stability of the Bcl-2/Bax complex. The importance of the Bcl-2/Bax interaction to the proliferation-restraining function of Bcl-2 is unknown.

Also, the region deleted in Bcl2Δ51-85 contains several Ser and Thr residues. It has been reported that Bcl-2 activity can be modulated by phosphorylation (34, 46, 47, and 49). Analysis of the activity of several Bcl-2 mutants containing amino acid substitutions at Ser or Thr residues, as described in Example 4, suggests that modulation of the proliferation-restraining activity by phosphorylation is possible. Alternative explanations to account for the mutant phenotype are also possible. The deleted region is rich in Ala and Pro residues. Substitution of Pro residues in two positions within the AP domain resulted in Bcl-2 mutants that permit enhanced cell proliferation. The possibility that these residues play some negative regulatory role in Bcl-2 activity remains to be investigated.

In one aspect then, the invention provides isolated oligonucleotides that encode the Bcl-2 AP domain or fragments of the domain. The oligonucleotides and short segments thereof are useful for screening for mutations in the Bcl-2 AP domain by methods known in the art, such as single strand conformational polymorphism (SSCP) and PCR mismatch analysis.

In another aspect, the present invention is directed to identifying protein/protein interactions between the Bcl-2 AP domain and known or as yet unidentified cellular proteins. The Bcl-2 AP domain is also useful in the identification and cloning of genes whose protein products interact with this domain in Bcl-2. The interacting proteins may play a role in modulation of cellular proliferation.

The present invention also relates to an isolated polypeptide that is the Bcl-2 AP domain and fragments of the domain. The domain may be a target for allosteric regulators of Bcl-2 function, such as protein kinases and/or phosphatases. Accordingly, peptides derived from this domain, prepared synthetically or as bacterially expressed fusion proteins, can be used as substrates to identify and characterize potential regulatory kinases and/or phosphatases.

The invention further provides screening methods to identify molecules that modulate the proliferation-restraining activity of the AP domain. In one aspect, such screening methods involve the effect of a putative modulating molecule on the short term or long term proliferation of cells in culture expressing the AP domain. In another aspect, putative modulating molecules can be identified by screening for agents that disrupt necessary protein/protein interactions mediated by the AP domain, using in vitro binding assays.

In yet another aspect, the invention provides for expression vectors containing genetic sequences, hosts transformed with such expression vectors, and methods for producing the AP domain and fragments of the domain that hinder or completely block proliferation.

In additional aspects, the present invention relates to antibodies that specifically bind to the AP domain and fragments of the domain that hinder or completely block cell proliferation. Peptides comprising the domain are useful for producing antibodies thereto. Such antibodies are useful for detecting and isolating proteins comprising the AP domain in biological specimens including, for example, cells from all human tissues including heart tissue, lung tissue, tumor cells, brain tissue, placenta, liver, skeletal muscle, kidney, and pancreas, as well as for modulating the proliferation-restraining activity of proteins comprising the AP domain, in and from such biological specimens, and constitute additional aspects of the invention.

BRIEF DESCRIPTION OF THE DRAWINGS

FIG. 2A shows an immunoprecipitation analysis of Bcl-2 and Bcl2Δ51-85 expression in BRK-p53val135-E1A cells. FIG. 2B is a graph showing survival/proliferation of BRK-p53val135-E1A cells at 32.5° C. ●, pRcCMV vector; ■, wt Bcl-2; ▲, Bcl2Δ51-85. FIGS. 2C–E show the growth of colonies of cells transfected with vectors carrying various Bcl-2 genes. The Figures illustrate the long-term proliferation of BRK-p53val135-E1 A cells. FIG. 2C, pRcCMV vector; FIG. 2D, wt Bcl-2; FIG. 2E, Bcl2Δ51-85.

FIG. 3A shows the results of an immunoprecipitation analysis of Bcl-2 and Bcl2Δ51-85 expression in Rat1MycER-Hygro cells. FIG. 3B is a graph showing survival/proliferation of RatMycER-Hygro cells. ●, pRcCMV vector; ■, wt Bcl-2; ▲, Bcl2Δ51-85.

DETAILED DESCRIPTION OF THE INVENTION

Figure 1:
FIG. 1 shows the domain structure of Bcl-2. The various conserved domains (BH1-4) are indicated. BH1-3 are conserved among both survival-promoting and death-promoting members of the Bcl-2 family of proteins. BH1 and 2 are described in ref. 33. BH3 is described in ref. 32. BH4 is conserved among survival-promoting members and corresponds to box A described by Reed and coworkers (ref. 38). TM indicates transmembrane domain. NH-1 indicates the E1B nineteen K homology domain (21). The amino acid sequence (SEQ ID NO:1) deleted in mutant Bcl2Δ51085 is indicated.

Isolated, in the context of the invention, indicates that some intervention occurs that increases the level of purity of a molecule over that found in nature.

As mentioned above, the present invention is based upon the discovery of a heretofore unidentified domain of the human Bcl-2 protein. This "anti-proliferation" or "AP" domain is required for modulation of cell proliferation. More specifically, the AP domain completely blocks cell proliferation.

The nucleotide sequence of human Bcl-2 according to this invention is based on those described in reference 41, Genbank Accession #X06487 and in reference 42, Genbank Accession #M13994. The Bcl-2 nucleotide sequence described in reference 41 has a G at position 189 and an A at position 287. The Bcl-2 nucleotide sequence described in reference 42 contains an alternate nucleotide (C in place of G) at position 189 and an alternate nucleotide (G in place of A) at position 287 resulting in an amino acid change at residue 96 of Thr to Ala. The nucleotide sequence for Bcl-2 reported by Cleary et al (51), Genbank Accession #M14745, contains an alternate nucleotide at position 175 (A in place of C), resulting in an amino acid change at residue 59 of Pro to Thr.

As used herein, the phrase "anti-proliferation (or AP) domain" means a truncated human Bcl-2 protein comprising amino acid residue 51 to any of amino acid residues 85–97. (SEQ ID NOS:1–13).

Thus, in addition to the core residues, i.e. residues 51 to any of amino acid residues 85–97, the AP domain can include stretches of 1 or more amino acids in the amino-terminal direction from residue 85 and/or 1 or more amino acids in the carboxyl-terminal direction from residue 97, provided that the protein is truncated. That is, the AP domain of the present invention is not intended to include the full-length Bcl-2 protein. For example, the AP domain can include the core residues, i.e., residue 51 to any of amino acid residues 85–97, and/or 5, 10, 15, 20 residues, and so on, in increments of 5 to the amino-terminus of residue 51 and/or carboxyl-terminus of residue 97.

The sequences of the polypeptide that make up the core residues, i.e. SEQ ID NOS: 1–13, are set forth in the section following the examples. The sequences of any additional stretches upstream or downstream of the core residues may be ascertained from the literature (E.G. 41, 42, 51) and protein databases such as EMBL.

Further, the data in Example 5 herein indicates that certain amino acids are needed to maintain full or partial anti-proliferation activity of the AP domain. For example, any one of Ser at position 51, Pro at position 57, Ser at position 62, Thr-Ser at positions 69 and 70, Thr at position 74, and Pro at position 75 may contribute to the anti-proliferation function of the AP domain which is lost when residues 51–85 are deleted. Thus, fragments of the AP domain that include any one or more of the residues that fully or partially restores anti-proliferation activity are within the present invention.

Functional equivalents of the polypeptide that make up the core residues as defined by SEQ ID NOS: 1–13 are also within the present invention. By "functional equivalent" is meant a peptide possessing a biological activity or immunological characteristic substantially similar to that of the polypeptides that make up the core residues, and is intended to include "variants", "analogs", "homologs", or "chemical derivatives" possessing such activity or characteristics. Functional equivalents of the polypeptides that make up the core residues, then, may not share an identical amino acid sequence, and conservative or non-conservative amino acid substitutions of conventional or unconventional amino acids are possible. However, in the present invention any of Ser at position 51, Pro at position 57, Ser at position 62, Thr and Ser at positions 69 and 70, Thr at position 74, or Pro at position 75, may not be Ala.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

Functional equivalents that possess immunological characteristics substantially similar to that of the polypeptides that make up the core residues are useful, for example, as an antigen for raising antibodies against the AP domain or fragments thereof or for detection or purification of antibodies against the AP domain or fragments thereof.

The nucleotide sequences that encode the AP domain as defined herein are also within the present invention. The nucleic acid compositions of the invention will generally be in RNA or DNA forms, mixed polymeric forms, or any synthetic nucleotide structure capable of binding in a base-specific manner to a complementary strand of nucleic acid. The described nucleic acid embodiment is typically derived from genomic DNA or cDNA, prepared by synthesis, or derived from combinations thereof, including polymerase chain reaction (PCR) products.

The oligonucleotides that encode the core amino acids are those bounded by nucleotide 151 to any of nucleotides 255–291 (SEQ ID NO: 14–50), where nucleotide 1 is the first nucleotide of the codon encoding the first amino acid of Bcl-2. In these sequences the nucleotide at position 175 can be C or A, the nucleotide at position 189 can be C or G, and the nucleotide at position 287 can be A or G.

The oligonucleotide sequences that encode the core residues, i.e. SEQ ID NOS: 14–50, are set forth in the section following the examples. The cDNA sequences toward the 5' end of nucleotide 151 and toward the 3' end of nucleotide 291 may be ascertained from the literature (E.G. 22, 42, 51) as well as from sequence databases such as Genbank.

Oligonucleotide fragments of oligonucleotide sequences that encode the AP domain are also included within the present invention and include fragments that contain at least one codon encoding an amino acid needed to maintain full or partial anti-proliferation activity of the AP domain. Examples are fragments that retain any one of the codons defined by nucleotides 151–153 (coding for Ser 51), 169–171 (coding for Pro 57), nucleotides 184–186 (coding for Ser 62), 204–210 (coding for Thr 69 and Ser 70), 220–222 (coding for Thr 74), and 223–225 (coding for Pro 75).

The instant oligonucleotides and polypeptides may be obtained as described herein, such as by recombinant means. For example, nucleotide sequences encoding the AP domain polypeptides or fragments thereof of the invention may be inserted into a suitable DNA vector, such as a plasmid, and the vector used to transform a suitable host. The recombinant AP polypeptide or fragment is produced in the host by expression. The transformed host may be a prokaryotic or eukaryotic cell, including a mammalian cell. The instant oligonucleotides and polypeptides may also be used to obtain homologous nucleic acids and proteins by hybridization, for example, an instant nucleic acid can be used as a probe of a gene bank to identify clones with suitable homology therewith. Also, within the confines of available technology, the oligonucleotides may be synthesized in vitro using, for example, solid phase oligonucleotide and oligopeptide synthetic methods known in the art.

The present invention also includes fusion polypeptides between the AP domain, or fragments thereof, or truncated wt Bcl-2 polypeptides including the AP domain, and other proteins or polypeptides. For example, fusions may include proteins that serve as purification targets, such as, but not limited to glutathione S-transferase (GST) (43) and the FLAG epitope tag (Eastman Kodak). In addition, fusions may include polypeptides that may have amino acid residues that have been or can be chemically modified by phosphorylation, biotinylation, acylation, or other moieties, using methods known in the art. Fusion polypeptides will typically be made by using either synthetic polypeptide or recombinant nucleic acid methods known in the art.

The functional importance of the AP domain is related to its ability to regulate cell proliferation. This regulation may be mediated by one or more protein/protein interactions between the domain and known Bcl-2 interacting proteins such as Bax (44), Nip 1-3 (29), Bik (32), Bak (31), R-ras (52), BAG-1 (45) and c-raf-1 (30) (see also Example 4) or as yet unidentified cellular proteins. The polypeptides of the present invention are useful to screen for proteins that interact with the AP domain, and these proteins and cDNA's encoding these proteins are also part of the invention. Such molecules are useful as agents for modulation of tumorigenesis and apoptotic activity of cells.

Methods for screening for proteins that interact with the AP domain are well known in the art and include the yeast two-hybrid system (39, 28) and expression cloning strategies using recombinant fusion proteins. (53, 54)

The in vivo genetic strategy designated 'two hybrid' cloning (39, 28) permits rapid genetic screening in yeast of molecules that associate, and the method has been used to isolate from expression libraries cDNA clones that code for proteins interacting with several known proteins.

Briefly, the method relies on the double transformation of yeast hosts with plasmids that encode fusion proteins. One plasmid carries partial sequences for a reporter molecule, for example, the GAL4 DNA binding domain, at the amino terminus of the fusion protein and sequences for the known protein, to which a ligand is sought, also known as the "bait" at the carboxyl-terminus. For example, the bait can be the AP domain polypeptide.

The second plasmid comprises sequences encoding a complementary protein for the reporter molecule, in the above case, required by the GAL4 DNA binding domain, such as the GAL4 activation domain, at the amino terminus and expressed products of individual cDNA from a bank at the carboxyl-terminus. A suitable host is used to enable the selection planned. In the scenario discussed, the host would be one wherein the expression of β-galactosidase is under the control of the GALL promoter.

Selection of double transformants are those that express β-galactosidase, hence would be blue colonies on an X-gal plate because the bait protein encoded by the cDNA of the second plasmid bind and that interaction juxtaposes the two GAL4 regulatory elements required for β-galactosidase expression.

An additional related strategy is to isolate positive clones from the two hybrid assay that interact with GAL4 DNA-binding domain-Bcl-2 (wt) fusion but not with a GAL4 DNA-binding domain-Bcl-2Δ51-85 fusion. Such interacting proteins may require the identified domain for their interaction.

Thus, the present invention provides a method for screening for a polypeptide that binds the AP domain of Bcl-2 protein, the method comprising:

(a) conducting a double transformation wherein one vector expresses a fusion protein comprising the AP domain or a fragment thereof and a reporter molecule and the other vector expresses a fusion protein comprising a complementary protein for the reporter molecule and the polypeptide to be screened;

(b) monitoring for activation of the reporter molecule; and (c) isolating cDNA that encodes the protein that binds to the AP domain or the fragment thereof, wherein the AP domain or fragment thereof is a truncated Bcl-2 protein comprising residues 51 to any of residues 85–97 (SEQ ID NOS:1–13) or a fragment thereof that contains at least one amino acid needed to maintain full or partial anti-proliferation activity of the AP domain.

In a related embodiment, the present invention also provides a method of screening for a polypeptide that binds the AP domain of Bcl-2 protein, the method comprising:

(a) conducting a first double transformation wherein one vector expresses a fusion protein comprising the AP domain and a reporter molecule and the other vector expresses a fusion protein comprising a complementary protein for the reporter molecule and the polypeptide to be screened;

(b) conducting a second double transformation wherein one vector expresses a fusion protein comprising Bcl-2 with the AP domain or a fragment of Bcl-2 that contains at least one amino acid needed to maintain full or partial anti-proliferation activity of the AP domain deleted and a reporter molecule and the other vector expresses a fusion protein comprising a complementary protein for the reporter molecule and the polypeptide to be screened;

(c) monitoring for activation of the reporter molecule in both double transformations; and (d) isolating cDNA that encodes a polypeptide that binds in step (a) but not in step (b).

In a second example of methods of screening for proteins that interact with the AP domain, a cDNA encoding Bcl-2 residues 51–85 is cloned into an *E. coli* expression vector that will encode a glutathione S-transferase (GST)-Bcl-2 domain fusion protein. The fusion protein is isolated following expression in bacteria and radiolabeled for use as a probe to screen for cDNA of proteins capable of interacting with the AP domain from a human cell λ-phage expression library. (53, 54) Briefly, a λ-phage expression library (e.g. λ-ZAP, Stratagene) is plated on *E.coli* and resulting plaques are transferred to isopropyl-β-D-thogalactoside (IPTG)-impregnated nitrocellulose filters to induce protein expression. $^{32}$P-radiolabeled GST-AP domain fusion proteins or unlabeled GST-AP domain fusion proteins that can be detected with an anti-GST antibody, are used as a probe to screen for expressed proteins capable of interacting with the AP domain. Positive clones can be isolated and the gene encoding a protein capable of interacting with the AP domain can be sequenced and characterized.

Thus, the present invention provides a method for screening for a polypeptide that interacts with the AP domain of Bcl-2 protein, the method comprising:

(a) expressing cDNA that encodes a polypeptide to be screened;

(b) immobilizing the expressed polypeptide; and (c) detecting interaction with a polypeptide comprising the AP domain or fragment thereof;

wherein the AP domain or fragment thereof is a truncated Bcl-2 protein comprising residues 51 to any of residues 85–97 (SEQ ID NOS:1–13) or a fragment thereof that contains at least one amino acid needed to maintain full or partial anti-proliferation activity of the AP domain.

Alternatively, the biochemical isolation of interacting molecules is also possible using isolated polypeptides comprising the Bcl-2 AP domain. For example, GST-AP domain fusion proteins can be immobilized on glutathione (GSH)-agarose columns to capture interacting proteins from cell lysates. Cell lysates from BRK-p53val135-E1A cells are passed over the column. Following washing to remove non-binding proteins, interacting proteins can be eluted using GSH or other conditions known to disrupt protein/protein interactions such as salt, pH, guanidine HCl, or detergent gradients. Eluted proteins can be identified, for example, by SDS-PAGE and microsequencing. If necessary, oligonucleotide probes based on the protein sequence can be used to clone the corresponding gene from an appropriate cDNA library.

Thus, the present invention provides a method for screening for a polypeptide that interacts with the AP domain of Bcl-2 protein, the method comprising:

(a) immobilizing a polypeptide comprising the AP domain or fragment of the AP domain;

(b) contacting the immobilized polypeptide with putative interacting protein; and (c) identifying interacting protein;

wherein the AP domain or fragment thereof is a truncated Bcl-2 protein comprising residues 51 to any of residues 85–97 (SEQ ID NOS:1–13) or a fragment thereof that contains at least one amino acid needed to maintain full or partial anti-proliferation activity of the AP domain.

The present invention includes the use of the AP domain or fragments for the identification of agents that modulate AP domain mediated functions. Such agents may include peptides comprising the AP domain or mutants of the AP domain or comprising an AP domain. A "mutant" as used herein refers to a peptide having an amino acid sequence that differs from the amino acid sequence of the naturally occurring peptide or protein by at least one amino acid. Mutants may have the same biological and immununological activity as the naturally occurring AP domain. However, the biological or immunological activity of mutants may differ or be lacking. Identification of such agents can be accomplished by the screening of peptide or compound libraries, or other information banks, in assays for agonists or antagonists that enhance or inhibit AP domain function, e.g. survival-promoting and proliferation-restraining activity, as well as protein binding.

For example, BRK-p53val135-E1A cells expressing Bcl-2 or a truncated version of Bcl-2 comprising the AP domain can be used to screen for agents that inhibit the proliferation-restraining activity the AP domain detected by increased proliferation in the short term assay and/or allowing colony formation in the long term assay.

In another example, agents can be identified that modulate the proliferation-restraining activity of the AP domain by screening for compounds that influence protein/protein interactions mediated by the AP domain using an in vitro binding assay. In such as an assay, a GST fusion protein comprising the AP domain is immobilized to GSH-agarose. Binding of a radiolabaled-interacting protein in the presence of one or more compounds to be tested would be quantitated by scintillation counting. Inhibitors of the interaction would result in a decrease in associated interacting protein. For rapid-throughput screening, the GST/AP-domain fusion protein and biotinylated interacting protein are used in a multi-well plate format. Biotinylated proteins can be expressed and isolated from $E.coli$ using PinPoint vectors (Promega) by known methods. The purified biotinylataed protein is immobilized on a neutravidin-coated plate and binding of the GST/Ap-domain fusion protein in the presence of test compounds is detected by ELISA using an anti-GST monoclonal antibody. Inhibitors of the interaction would score as a decreased ELISA signal.

A high speed screen using immobilized or "tagged" combinatorial libraries can be used to identify agents that bind directly to the AP domain. Such agents are candidates to be tested for their ability to enhance or inhibit the proliferation-restraining activity of Bcl-2.

The AP domain may be a target for allosteric regulators of Bcl-2 function such as protein kinases and/or phosphatases. Phosphorylation of Bcl-2 has been reported (46–49) and it has been suggested that phosphorylation/dephosphorylation may play a role in the regulation of Bcl-2 function. The identified domain of Bcl-2 contains several potential phosphorylation sites. Thus, the polypeptides of the present invention comprising the AP domain can be used as substrates to measure an enzymatic activity, such as kinase or phosphatase. In this aspect, in vitro kinase assays are carried out by incubating cell lysates, such as derived from BRK-p53val135-E1A cells, with AP domain polypeptides, prepared synthetically or as bacterially expressed fusion proteins, in the presence of $^{23}$P-labeled ATP in 10 mM Tris buffer containing 10 mM $MgCl_2$ and 1 $\mu$M unlabeled ATP. Phosphatase activity is detected by incubating cell lysates with phosphorylated AP domain polypeptide, derived from in vitro kinase assays described above or isolated from cells, and following the release of radiolabeled phosphate from the AP domain. Purification and sequencing of the protein responsible for this activity can be accomplished by standard methods such as those described in "Protein Purification: Principles and Practice," by Robert Scopes (Ed: C. Cantor, Springer Verlag, Heidelberg, 1982).

Synthetic peptides or fusion proteins containing this domain can be used for immunizing animals in the production of polyclonal or monoclonal antibodies that bind to this domain in Bcl-2. Such antibodies would be useful as reagents for studying the function of this domain. For example, microinjection of anti-domain antibodies may alter the cell cycle arrest activity of Bcl-2. Such antibodies may also prove to be useful in screening for mutations in this domain of Bcl-2 that cause alterations in antibody binding. These mutations may correlate with alterations in Bcl-2 function.

The AP polypeptides of the invention also may be used for the detection of Bcl-2 by means of standard assays including radioimmunoassays and enzyme immunoassays.

The polypeptides of the present invention or fusion proteins thereof are also useful to make antibodies for detection or determination of proteins comprising the AP domain, for example, in fractions from tissue/organ excisions, by means of immunochemical or other techniques in view of the antigenic properties thereof. Immunization of animals with polypeptides comprising the AP domain alone or in conjunction with adjuvants by known methods can produce antibodies specific for the AP domain polypeptide. Antiserum obtained by conventional procedures may be utilized for this purpose. For example, a mammal, such as a rabbit, may be immunized with a peptide comprising the AP domain, thereby inducing the formation of polyclonal antibodies thereagainst. Monoclonal antibodies also may be generated using known procedures.

If the target molecule is poorly immunogenic, known methods for enhancing immunogenicity, such as, use of adjuvants, use of fragments of the target molecule as antigen, conjugating the target molecule or fragments thereof to a known carrier, such as albumin or keyhole limpet hemocyanin, immunizing immune cells in vitro and the like, as known in the art can be used.

Antibodies against the AP domain polypeptides or fragments thereof of the invention may be used to screen cDNA expression libraries for identifying clones containing cDNA inserts encoding structurally related, immunocrossreactive proteins that may be members of an AP domain family of proteins. Screening of cDNA and mRNA expression libraries is known in the art. Similarly, antibodies against AP domain polypeptides or fragments thereof can be used to identify or purify immunocrossreactive proteins related to this domain, or to detect or determine the amount of proteins containing the AP domain in a cell or cell population, for example, in tissue or cells, such as lymphocytes, obtained from a patient. Known methods for such measurements include immunopreciptiation of cell extracts followed by PAGE, in situ detection by immunohistochemical methods, and ELISA methods, all of which are well know in the art. In addition, antibodies against the AP domain or fragments thereof may be used to modulate the proliferation-restraining activity of proteins comprising the AP domain.

Accordingly, the present invention also provides an isolated antibody that binds to the AP domain of Bcl-2 and a hybridoma that makes monoclonal antibody that specifically binds to the AP domain.

The cDNA of the present invention may be used for screening for mutations in the AP domain in, for example, human tumors. Indeed, mutations within this domain associated with non-Hodgkin's lymphomas have been reported including a change in the nucleotide (T in place of C) at position 175 resulting in a substitution of Pro 59 with Ser (50).

Methods for screening for such mutations have been described, and include single strand conformational polymorphism (SSCP) of polymerase chain reaction-amplified DNA fragments (SSPC-PCR) (55, 56) and PCR-mismatch analysis (50, 51).

In SSCP-PCR, oligonucleotide primers are used to amplify the segment of the Bcl-2 gene encoding the AP domain from DNA or mRNA isolated from a test sample or from cDNA made from the test sample. The PCR product is then heat denatured, subjected to electrophoresis on polyacrylamide gels and transferred to a nylon membrane. The fragment can be detected by a chemiluminescence detection system and the relative mobility of the test fragment with a control fragment from wt Bcl-2 is determined. A single base change can be detected by this method.

Accordingly, the present invention provides a method of screening for mutations in the AP domain of Bcl-2, the method comprising:

(a) isolating genomic DNA, cDNA or mRNA from a specimen to be screened;

(b) amplifying DNA fragments encoding the AP domain or portions thereof from the genomic DNA, cDNA or mRNA;

(c) denaturing the amplified product;

(d) subjecting the denatured product to electrophoresis; and (e) detecting mutations by comparing the mobility of the denatured amplified product to a control DNA encoding the AP domain or portions thereof corresponding positionally to the DNA fragments amplified in step (b);

wherein the control DNA encoding the AP domain or portions thereof is from the truncated cDNA encoding the bcl-2 gene and fragments of the truncated cDNA.

Alternatively, in PCR-mismatch analysis, PCR products from the test sample are mixed with radiolabeled PCR products from the wild type Bcl-2 AP domain. The mixed PCR material is denatured and then annealed. Chemical modification and cleavage of heteroduplexes containing mismatched nucleotides is analyzed by gel electrophoresis. PCR-generated DNAs containing mutations are then subcloned and sequenced to identify the precise nature of the mutation.

Thus, the present invention provides a method of screening for mutations in the AP domain of Bcl-2, said method comprising:

(a) isolating genomic DNA, cDNA or mRNA from a specimen to be screened;

(b) amplifying DNA fragments encoding the AP domain or portions thereof from the genomic DNA, cDNA or mRNA;

(c) mixing the amplified product with labeled PCR product from the corresponding position in a control AP domain or portion thereof;

(d) denaturing and annealing the mixed PCR products; and (e) analyzing for mismatched nucleotides by electrophoresis following chemical modification;

wherein the control DNA encoding the AP domain or portions thereof is selected from the truncated cDNA encoding the bcl-2 gene and fragments of the truncated cDNA.

In a related embodiment, the present invention also provides a method of screening for mutations in the AP domain of Bcl-2, said method comprising:

(a) isolating genomic DNA, cDNA or mRNA from a specimen to be screened;

(b) amplifying DNA fragments encoding the AP domain or portions thereof from the genomic DNA, cDNA or mRNA; and (c) sequencing the amplified DNA product.

Of course, the polynucleotide sequences of the invention may be used in the PCR method to detect the presence of mRNA encoding AP domain polypeptides in for, example, cells from all human tissues including heart tissue, lung tissue, tumor cells, brain tissue, placenta, liver, skeletal muscle, kidney, and pancreas.

EXAMPLES

The invention will now be described by means of working examples that are not intended to be limiting.

Materials and Methods

Plasmids. Plasmid pRcCMV-Bcl-2 was constructed by cloning the human bcl-2 gene (22) into the HindIII and XbaI sites of the mammalian expression vector pRcCMV (Invitrogen). Mutant Bcl2Δ51-85 was constructed by PCR mutagenesis using a mutagenic oligonucleotide primer 5'-GGA-CCA-CAG-GTG-GCA-CCG-GGC-TGA-GGC-TAG-CGG-AGA-AGA-AGC-CCG-GTG-CGG-GGG-CG-3' (SEQ ID NO:51 ) and two other primers complementary to the 5' and 3' ends of bcl-2. This mutagenesis introduces an NheI site, and substitutes an alanine and a serine residue in the deleted region. The PCR product was cloned into the HindIII and XbaI sites of pRcCMV to generate pRcCMV-Bcl2Δ51-85. pTM1-based plasmids expressing wt Bcl-2 and mutant Bcl2Δ51-85 were constructed by cloning the respective genes into the NcoI and SalI sites of the vector pTM1 (23).

Cell lines.

The BRK-p53val135-E1A cell line has been described (21) and was maintained at 38.5° C. in Dulbecco's modified Eagle medium (DMEM) supplemented with 10% fetal calf serum. BRK-p53val135-E1A cells stably expressing Bcl-2 were generated by transfection of various pRcCMV-based Bcl-2 expression plasmids and selection with G418 (250 µg/ml)(GIBCO/BRL). Rat1a and Rat1MycER-Hygro cells have been described (14,24). Cells expressing ER fusion proteins were maintained in DMEM media without phenol red and 10% fetal calf serum (certified low estrogen content, GIBCO/BRL). Rat1MycER-Hygro cells expressing Bcl-2 were selected by transfection with pRcCMV-Bcl2 or pRcCMV-Bcl2Δ51-85 and selection with 400 µg/ml G418. DNA transfections were carried out by the standard calcium phosphate method.

Cell death assays.

BRK-p53val135-E1A cells were plated at $5\times10^5$ cells/35 mm dish. After 12 hours at 38.5° C., the dishes were shifted to 32.5° C., and at various intervals cells were trypsinized in triplicates, stained with 0.2% trypan blue and viable cells were counted. Similarly $5\times10^5$ Rat1-Hygro cells were plated in 35mm dishes, incubated for 12 hours at 37° C., washed three times in serum-free DMEM and maintained in fresh media containing 0.1% fetal calf serum and 1 µM β-estradiol. Viable cell number was determined at various intervals.

Immunoprecipitation.

Bcl-2 or Bcl2Δ51-85 proteins were co-expressed with HA epitope-tagged Bax using the vaccinia virus/T7 coupled expression system as previously described (29). BSC40 cells were transfected with pTM1 expression plasmids using LipofectAMINE (GIBCO/BRL) and infected with the recombinant vaccinia virus vTF7-3 (23) expressing the T7 RNA polymerase. Sixteen hours post-infection, cells were metabolically labeled with 500 µCi of $^{35}$S-methionine and -cysteine mixture for two hours and lysed in isotonic buffer (29) containing protease inhibitors (0.04 mg/ml aprotinin, 0.2 mg/ml leupeptin, 200 μM phenylmethylsulfonyl fluoride). Lysates were precleared with protein A-Sepharose for 1 hour, which was removed by centrifugation. The proteins were immunoprecipitated with a rabbit polyclonal antibody specific for human Bcl-2 or with HA monoclonal antibody (12CA5; Boehringer Mannheim). The proteins were analyzed by electrophoresis on 13% SDS polyacrylamide gels and detected by fluorography.

Example: 1

Effect on P53-induced Apoptosis

Figure 2A:
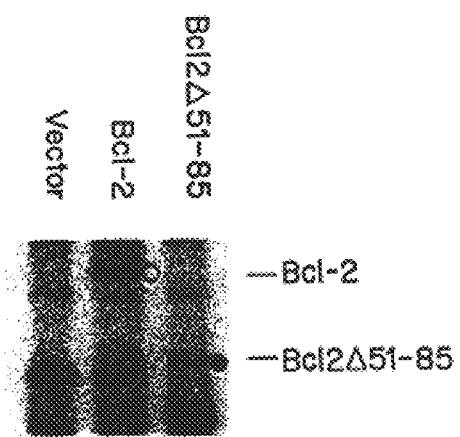
FIGS. 2A to 2E illustrate suppression of p53-induced apoptosis by Bcl-2.
Figure 2B:
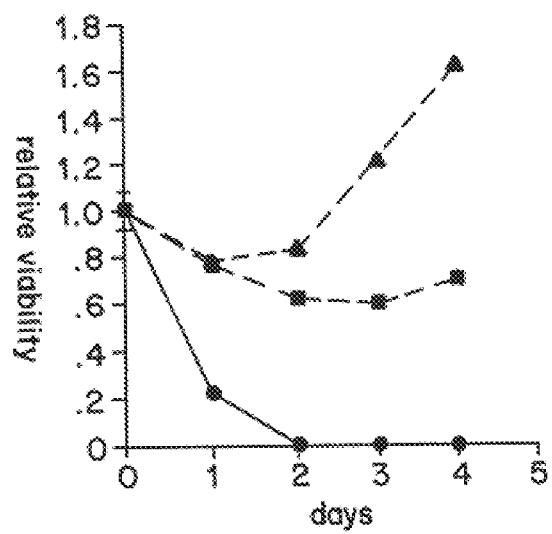
Figure 5:
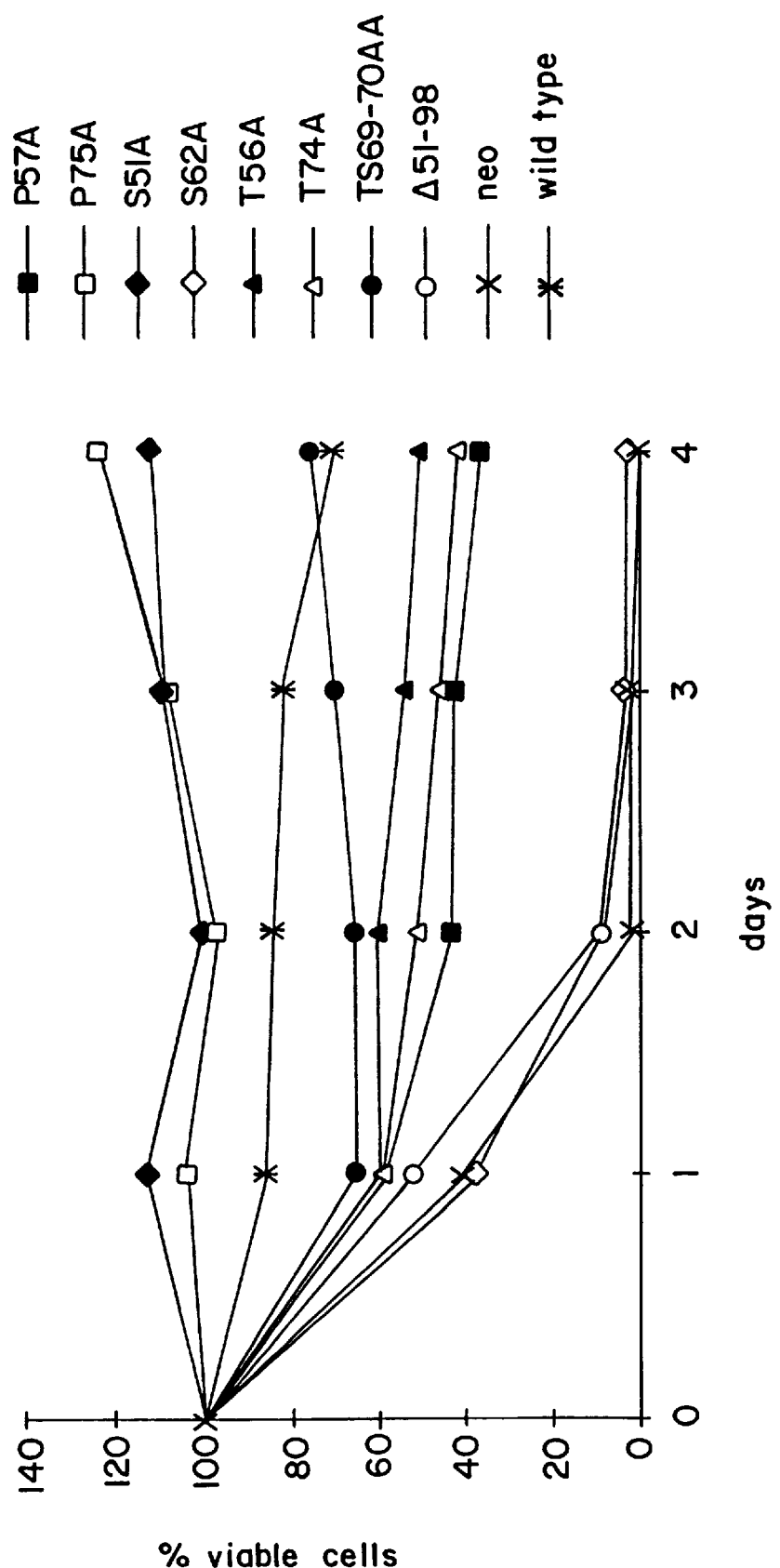
FIG. 5 is a graph showing survival of BRK-p53val153-E1A cells expressing point mutants of Bcl-2. The number of viable cells was determined at various times after shifting to 32.5° C. by trypan blue exclusion and is plotted as a percentage of the number of live cells at the start of the experiment.

A non-conserved region located between residues 51 and 85 was examined (FIG. 1) with the rationale that such sequences may regulate the activity of Bcl-2. Deletion of this region of Bcl-2 (Bcl2Δ51-85) did not significantly alter the level of expression of the mutant protein (FIGS. 2A; 3A). The effect of Bcl-2 wt and mutant Bcl2Δ51-85 on apoptosis induced by the tumor suppressor protein p53 (25) was tested. Baby rat kidney (BRK) cells transformed with adenovirus E1A and a ts mutant of p53 (p53val135) (26) express very high levels of mutant p53 at the non-permissive (38.5° C.) temperature and undergo rapid apoptosis after the p53 protein assumes wt conformation at 32.5° C. (27). This apoptosis can be efficiently suppressed by Bcl-2 (20). BRK-p53val135-E1A cells were transfected with pRcCMV vector or pRcCMV-Bcl-2 or pRcCMV-Bcl2Δ51-85 and G418 resistant colonies were selected at 38.5° C. As expected, wt Bcl-2 efficiently suppressed cell death compared to cells transfected with pRcCMV vector (FIG. 2A). Cells expressing Bcl2Δ51-85 did not lose cell viability significantly at 32.5° C. Surprisingly, however, these cells also proliferated efficiently at this temperature in contrast to cells expressing wt Bcl-2 (FIG. 2B). Deletion of additional residues, form 51–98, resulted in a mutant, Bcl-2Δ51-98 that was unable to suppress cell death in this assay (FIG. 5, Table 1) suggesting that residues between 85 and 98 may be critical for Bcl-2 survival function.

Figure 2C:
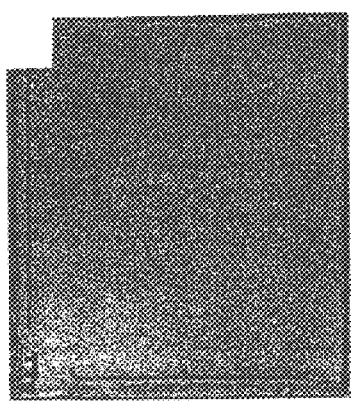
Figure 2D:
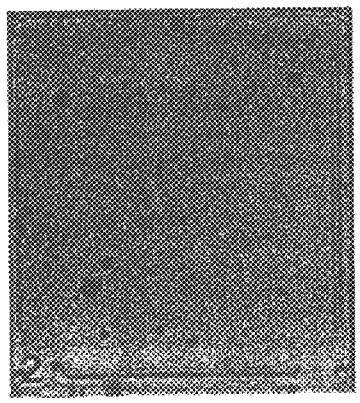
Figure 2E:
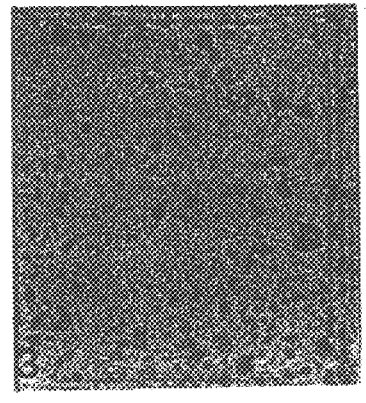

The effect of mutant Bcl2Δ51-85 on long term proliferation was also determined. Pooled cell lines transfected with Bcl-2 wt or Bcl2Δ51-85 or pRcCMV vector were plated at low cell density, maintained at 32.5° C. for three weeks and stained with Giemsa (FIGS. 2C–2E). Cells tranfected with pRcCMV died rapidly without forming any detectable colonies. Cells tranfected with wt Bcl-2 survived for an extended period, but formed very few proliferating colonies. Consistent with their behavior in short term cell survival/proliferation assays (FIG. 2B), cells transfected with mutant Bcl2Δ51-85 formed numerous proliferating colonies. These results indicate that the mutant Bcl2Δ51-85 facilitates long term proliferation of cells under conditions that otherwise result in apoptosis.

Example 2

Effect on Myc-induced Apoptosis

Figure 3A:
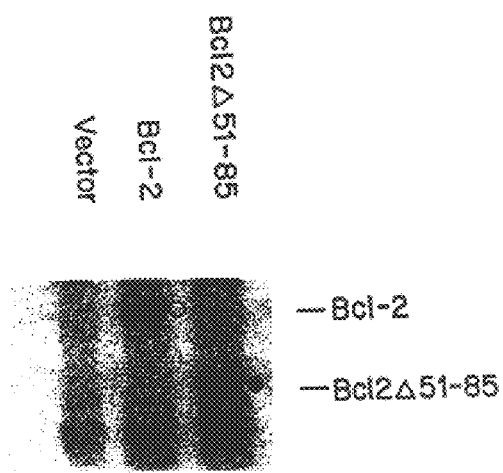
FIGS. 3A and 3B show suppression of Myc-induced apoptosis by Bcl-2.
Figure 3B:
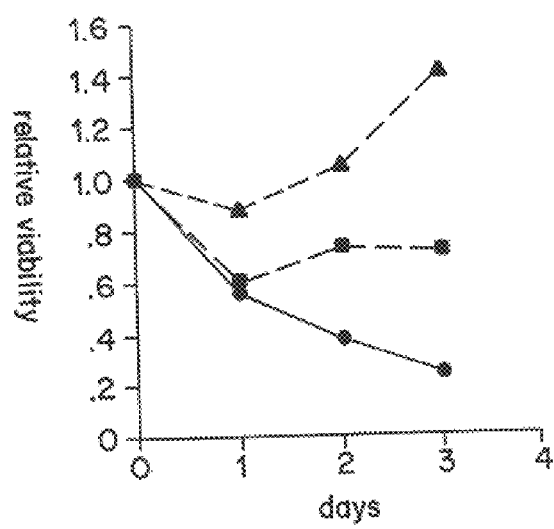

The effect of Bcl2Δ51-85 on Myc-induced apoptosis was also tested. Rat1 cells expressing the c-myc gene fused to the human estrogen receptor (c-mycER-Hygro) undergo apoptosis after Myc expression is activated by addition of 8-estradiol and cells are deprived of serum (13,14). The c-mycER-Hygro cells were tranfected with pRcCMV vector or pRcCMV-based plasmids expressing wt Bcl-2 or mutant Bcl2Δ51-85 and pooled G418-resistant cell lines were established. Immunoprecipitation (FIG. 3A) and protein-blot (not shown) analyses revealed that the various Rat1 cell lines expressed comparable levels of wt or the mutant Bcl-2 proteins. The effect of Bcl-2 expression on Myc-induced apoptosis was then determined by treating the cells with 1 μM β-estradiol in media containing 0.1% fetal calf serum. Deregulated Myc expression induced significant cell death. Expression of wt Bcl-2 resulted in about 60% cell survival. As in the case of BRK/p53val135-E1A cells, the expression of Bcl2Δ51-85 mutant not only suppressed cell death but also induced significant proliferation on mycER-Hygro cells in low serum after a lag period of about one day.

Example 3

Interaction of Cellular Proteins with Bcl2Δ51-85

Figures 4A, 4B:
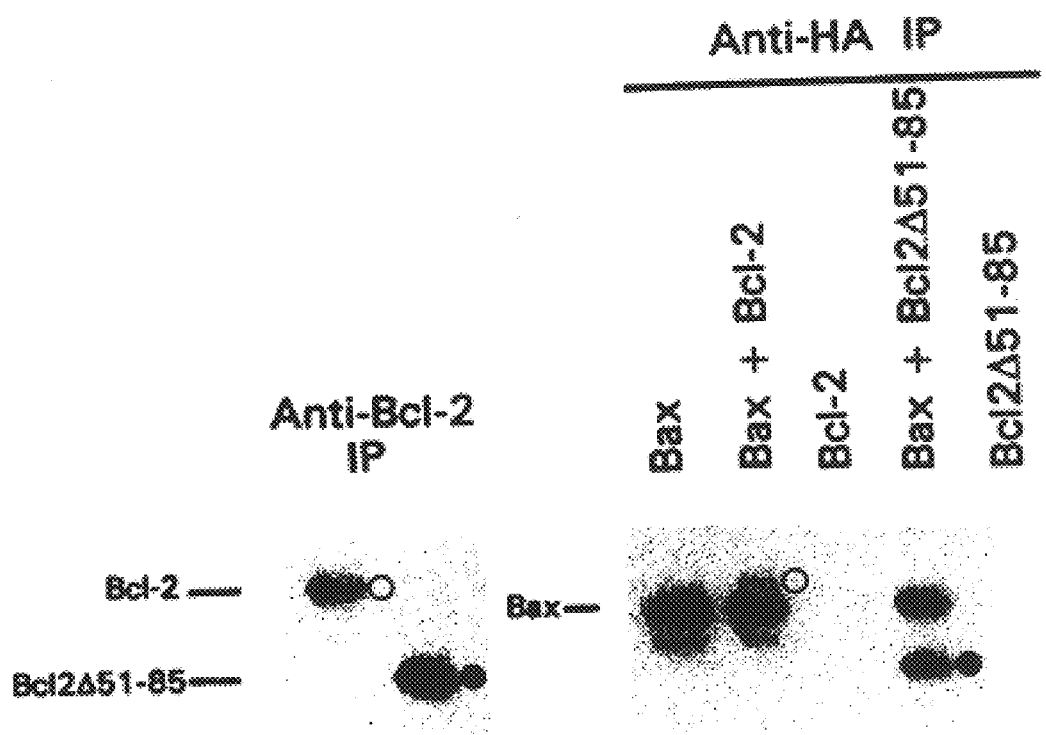
FIGS. 4A and B show the interaction of Bax with Bcl-2 and Bcl2Δ51-85. BSC40 cells were transfected with pTM-HA Bax and pTM-Bcl-2 or pTM-Bcl2Δ51-85 and infected with vaccinia virus vTF7-3. $^{35}$S-labeled proteins were immunoprecipitated either with HA mouse monoclonal antibody (FIG. 4A) or Bcl-2 rabbit polyclonal antibody (FIG. 4B) and analyzed on 13% SDS-polyacrylamide gels.

In order to determine if deletion of the amino acid region encompassing residues 51–85 affected interaction of various cellular proteins, the interaction of several cellular proteins that have been previously reported to interact with Bcl-2 either by two-hybrid interaction studies in yeast (28) or by co-immunoprecipitation analyses was examined. In these studies, no major difference was observed in the patterns of interaction of Nip 1-3 (29), c-Raf-1 (30), R-ras (52), Bak (31), and Bik (32) (not shown). In contrast, the level of interaction between Bax (33) and Bcl2Δ51-85 appeared to be significantly enhanced in comparison to wt Bcl-2 in co-immunoprecipitation assays (FIGS. 4A and 4B). This enhanced interaction appears to be significant considering that the total level of Bax was similar in cells expressing either Bcl2Δ51-85 or wt Bcl-2.

Example 4

Characterization of Critical Residues within the Bcl-2 Residue 51-85 Domain

In an effort to characterize critical residues within the Bcl-2 residue 51-85 domain, several Bcl-2 mutants encoding single amino acid substitutions were constructed and tested for their effect on cell survival and proliferation. In the short term survival assay (FIG. 5 and Table 1), none of the point mutants gave an enhanced proliferation activity comparable to the Bcl-2Δ51-85 mutant, though two mutants, P75A and S51A, had some effect. While most of the point mutations resulted in Bcl-2 molecules that retained at least significant survival function, substitution of serine at position 62 with alanine completely abolished survival activity. This result demonstrates that this region has substantial influence on the survival function of Bcl-2 as well as modulation of proliferation. In the long term assay (Table 1), several of the point mutants permitted significant colony formation, suggesting that these residues may contribute to the proliferation-restraining activity of Bcl-2. One substitution mutant, S51A, had a hyperprotective effect that was apparent in the long term assay. With wild type Bcl-2, the BRK-p53val135-E1A cells eventually die when subjected to the prolonged exposure at 32.5° C. used in the long term assay. In contrast, cells expressing Bcl-2 S51A survived for the duration of the assay, though no significant colony formation was observed.

TABLE 1

Comparison of survival activity and long term colony formation for Bcl-2 mutants. Survival activity and long-term proliferation (colony formation) was measured in BRK-p53val135-E1A cells at 32.5° C. as described for FIG. 2. Δ indicates deleted residues, substitution mutations (such as S51A) are indicated by the amino acid changed followed by the position number and the substituted amino acid. For survival activity, + is normal +\- is partial, ++ and +++ are above normal. For colony formation, + is small, ++ is medium, +++ is large colonies. Mat indicates that cells were present without obvious colony formation. -, indicates no cells remaining.

| Bcl-2 mutant | Survival Activity | colony formation |
|---|---|---|
| vector | - | - |
| wild type | + | - |
| Δ51-85 | ++ | +++ |
| Δ51-98 | - | - |
| S51A | +++ | mat |
| T56A | +\- | - |
| P57A | +\- | + |
| S62A | - | - |
| TS69-70AA | +\- | + |
| T74A | +\- | ++ |
| P75A | ++ | + |

A straightforward interpretation of these results is that the effect of the Bcl-2Δ51-85 mutant is a sum of the hyperproliferative function of the S51A mutant and the proliferative effects of the P57A, TS69-70AA, T74A, and P75A mutants.

SEQUENCES

Polypeptide and nucleotide sequences referred to herein by SEQ ID NOS. are listed below.

In the polypeptide sequences (Pro/Thr) and (Thr/Ala) means that the amino acid at that position can be Pro or Thr and Thr or Ala, respectively.

In the nucleic acid sequences M represents A or C, S represents C or G, and R represents A or G.

```
Ser Gln Pro Gly His Thr Pro His(Pro/Thr)Ala Ala Ser Arg Asp Pro Val Ala Arg Thr Ser        (SEQ ID NO:1)
Pro Leu Gln Thr Pro Ala Ala Pro Gly Ala Ala Ala Gly Pro Ala.

Ser Gln Pro Gly His Thr Pro His(Pro/Thr)Ala Ala Ser Arg Asp Pro Val Ala Arg Thr Ser        (SEQ ID NO:2)
Pro Leu Gln Thr Pro Ala Ala Pro Gly Ala Ala Ala Gly Pro Ala Leu.

Ser Gln Pro Gly His Thr Pro His(Pro/Thr)Ala Ala Ser Arg Asp Pro Val Ala Arg Thr Ser        (SEQ ID NO:3)
Pro Leu Gln Thr Pro Ala Ala Pro Gly Ala Ala Ala Gly Pro Ala Leu Ser.

Ser Gln Pro Gly His Thr Pro His(Pro/Thr)Ala Ala Ser Arg Asp Pro Val Ala Arg Thr Ser        (SEQ ID NO:4)
Pro Leu Gln Thr Pro Ala Ala Pro Gly Ala Ala Ala Gly Pro Ala Leu Ser Pro.

Ser Gln Pro Gly His Thr Pro His(Pro/Thr)Ala Ala Ser Arg Asp Pro Val Ala Arg Thr Ser        (SEQ ID NO:5)
Pro Leu Gln Thr Pro Ala Ala Pro Gly Ala Ala Ala Gly Pro Ala Leu Ser Pro Val.

Ser Gln Pro Gly His Thr Pro His(Pro/Thr)Ala Ala Ser Arg Asp Pro Val Ala Arg Thr Ser        (SEQ ID NO:6)
Pro Leu Gln Thr Pro Ala Ala Pro Gly Ala Ala Ala Gly Pro Ala Leu Ser Pro Val Pro.

Ser Gln Pro Gly His Thr Pro His(Pro/Thr)Ala Ala Ser Arg Asp Pro Val Ala Arg Thr Ser        (SEQ ID NO:7)
Pro Leu Gln Thr Pro Ala Ala Pro Gly Ala Ala Ala Gly Pro Ala Leu Ser Pro Val Pro Pro.

Ser Gln Pro Gly His Thr Pro His(Pro/Thr)Ala Ala Ser Arg Asp Pro Val Ala Arg Thr Ser        (SEQ ID NO:8)
Pro Leu Gln Thr Pro Ala Ala Pro Gly Ala Ala Ala Gly Pro Ala Leu Ser Pro Val Pro Pro
Val.

Ser Gln Pro Gly His Thr Pro His(Pro/Thr)Ala Ala Ser Arg Asp Pro Val Ala Arg Thr Ser        (SEQ ID NO:9)
Pro Leu Gln Thr Pro Ala Ala Pro Gly Ala Ala Ala Gly Pro Ala Leu Ser Pro Val Pro Pro
Val Val.

Ser Gln Pro Gly His Thr Pro His(Pro/Thr)Ala Ala Ser Arg Asp Pro Val Ala Arg Thr Ser        (SEQ ID NO:10)
Pro Leu Gln Thr Pro Ala Ala Pro Gly Ala Ala Ala Gly Pro Ala Leu Ser Pro Val Pro Pro
Val Val His.

Ser Gln Pro Gly His Thr Pro His(Pro/Thr)Ala Ala Ser Arg Asp Pro Val Ala Arg Thr Ser        (SEQ ID NO:11)
```

Pro Leu Gln Thr Pro Ala Ala Pro Gly Ala Ala Ala Gly Pro Ala Leu Ser Pro Val Pro Pro

Val Val His Leu.

Ser Gln Pro Gly His Thr Pro His(Pro/Thr)Ala Ala Ser Arg Asp Pro Val Ala Arg Thr Ser  (SEQ ID NO:12)

Pro Leu Gln Thr Pro Ala Ala Pro Gly Ala Ala Ala Gly Pro Ala Leu Ser Pro Val Pro Pro

Val Val His Leu(Thr/Ala).

Ser Gln Pro Gly His Thr Pro His(Pro/Thr)Ala Ala Ser Arg Asp Pro Val Ala Arg Thr Ser  (SEQ ID NO:13)

Pro Leu Gln Thr Pro Ala Ala Pro Gly Ala Ala Ala Gly Pro Ala Leu Ser Pro Val Pro Pro

Val Val His Leu(Thr/Ala)Leu.

TCCCAGCCCG GGCACACGCC CCATMCAGCC GCATCCCGSG ACCCGGTCGC  (SEQ ID NO:14)

CAGGACCTCG CCGCTGCAGA CCCCGGCTGC CCCCGGCGCC GCCGCGGGGC

CTGC

TCCCAGCCCG GGCACACGCC CCATMCAGCC GCATCCCGSG ACCCGGTCGC  (SEQ ID NO:15)

CAGGACCTCG CCGCTGCAGA CCCCGGCTGC CCCCGGCGCC GCCGCGGGGC

CTGCG

TCCCAGCCCG GGCACACGCC CCATMCAGCC GCATCCCGSG ACCCGGTCGC  (SEQ ID NO:16)

CAGGACCTCG CCGCTGCAGA CCCCGGCTGC CCCCGGCGCC GCCGCGGGGC

CTGCGC

TCCCAGCCCG GGCACACGCC CCATMCAGCC GCATCCCGSG ACCCGGTCGC  (SEQ ID NO:17)

CAGGACCTCG CCGCTGCAGA CCCCGGCTGC CCCCGGCGCC GCCGCGGGGC

CTGCGCT

TCCCAGCCCG GGCACACGCC CCATMCAGCC GCATCCCGSG ACCCGGTCGC  (SEQ ID NO:18)

CAGGACCTCG CCGCTGCAGA CCCCGGCTGC CCCCGGCGCC GCCGCGGGGC

CTGCGCTC

TCCCAGCCCG GGCACACGCC CCATMCAGCC GCATCCCGSG ACCCGGTCGC  (SEQ ID NO:19)

CAGGACCTCG CCGCTGCAGA CCCCGGCTGC CCCCGGCGCC GCCGCGGGGC

CTGCGCTCA

TCCCAGCCCG GGCACACGCC CCATMCAGCC GCATCCCGSG ACCCGGTCGC  (SEQ ID NO:20)

CAGGACCTCG CCGCTGCAGA CCCCGGCTGC CCCCGGCGCC GCCGCGGGGC

CTGCGCTCAG

TCCCAGCCCG GGCACACGCC CCATMCAGCC GCATCCCGSG ACCCGGTCGC  (SEQ ID NO:21)

CAGGACCTCG CCGCTGCAGA CCCCGGCTGC CCCCGGCGCC GCCGCGGGGC

CTGCGCTCAG C

TCCCAGCCCG GGCACACGCC CCATMCAGCC GCATCCCGSG ACCCGGTCGC  (SEQ ID NO:22)

CAGGACCTCG CCGCTGCAGA CCCCGGCTGC CCCCGGCGCC GCCGCGGGGC

CTGCGCTCAG CC

TCCCAGCCCG GGCACACGCC CCATMCAGCC GCATCCCGSG ACCCGGTCGC  (SEQ ID NO:23)

CAGGACCTCG CCGCTGCAGA CCCCGGCTGC CCCCGGCGCC GCCGCGGGGC

CTGCGCTCAG CCC

TCCCAGCCCG GGCACACGCC CCATMCAGCC GCATCCCGSG ACCCGGTCGC  (SEQ ID NO:24)

CAGGACCTCG CCGCTGCAGA CCCCGGCTGC CCCCGGCGCC GCCGCGGGGC

```
CTGCGCTCAG CCCG

TCCCAGCCCG GGCACACGCC CCATMCAGCC GCATCCCGSG ACCCGGTCGC            (SEQ ID NO:25)

CAGGACCTCG CCGCTGCAGA CCCCGGCTGC CCCCGGCGCC GCCGCGGGGC

CTGCGCTCAG CCCGG

TCCCAGCCCG GGCACACGCC CCATMCAGCC GCATCCCGSG ACCCGGTCGC            (SEQ ID NO:26)

CAGGACCTCG CCGCTGCAGA CCCCGGCTGC CCCCGGCGCC GCCGCGGGGC

CTGCGCTCAG CCCGGT

TCCCAGCCCG GGCACACGCC CCATMCAGCC GCATCCCGSG ACCCGGTCGC            (SEQ ID NO:27)

CAGGACCTCG CCGCTGCAGA CCCCGGCTGC CCCCGGCGCC GCCGCGGGGC

CTGCGCTCAG CCCGGTG

TCCCAGCCCG GGCACACGCC CCATMCAGCC GCATCCCGSG ACCCGGTCGC            (SEQ ID NO:28)

CAGGACCTCG CCGCTGCAGA CCCCGGCTGC CCCCGGCGCC GCCGCGGGGC

CTGCGCTCAG CCCGGTGC

TCCCAGCCCG GGCACACGCC CCATMCAGCC GCATCCCGSG ACCCGGTCGC            (SEQ ID NO:29)

CAGGACCTCG CCGCTGCAGA CCCCGGCTGC CCCCGGCGCC GCCGCGGGGC

CTGCGCTCAG CCCGGTGCC

TCCCAGCCCG GGCACACGCC CCATMCAGCC GCATCCCGSG ACCCGGTCGC            (SEQ ID NO:30)

CAGGACCTCG CCGCTGCAGA CCCCGGCTGC CCCCGGCGCC GCCGCGGGGC

CTGCGCTCAG CCCGGTGCCA

TCCCAGCCCG GGCACACGCC CCATMCAGCC GCATCCCGSG ACCCGGTCGC            (SEQ ID NO:31)

CAGGACCTCG CCGCTGCAGA CCCCGGCTGC CCCCGGCGCC GCCGCGGGGC

CTGCGCTCAG CCCGGTGCCA C

TCCCAGCCCG GGCACACGCC CCATMCAGCC GCATCCCGSG ACCCGGTCGC            (SEQ ID NO:32)

CAGGACCTCG CCGCTGCAGA CCCCGGCTGC CCCCGGCGCC GCCGCGGGGC

CTGCGCTCAG CCCGGTGCCA CC

TCCCAGCCCG GGCACACGCC CCATMCAGCC GCATCCCGSG ACCCGGTCGC            (SEQ ID NO:33)

CAGGACCTCG CCGCTGCAGA CCCCGGCTGC CCCCGGCGCC GCCGCGGGGC

CTGCGCTCAG CCCGGTGCCA CCT

TCCCAGCCCG GGCACACGCC CCATMCAGCC GCATCCCGSG ACCCGGTCGC            (SEQ ID NO:34)

CAGGACCTCG CCGCTGCAGA CCCCGGCTGC CCCCGGCGCC GCCGCGGGGC

CTGCGCTCAG CCCGGTGCCA CCTG

TCCCAGCCCG GGCACACGCC CCATMCAGCC GCATCCCGSG ACCCGGTCGC            (SEQ ID NO:35)

CAGGACCTCG CCGCTGCAGA CCCCGGCTGC CCCCGGCGCC GCCGCGGGGC

CTGCGCTCAG CCCGGTGCCA CCTGT

TCCCAGCCCG GGCACACGCC CCATMCAGCC GCATCCCGSG ACCCGGTCGC            (SEQ ID NO:36)

CAGGACCTCG CCGCTGCAGA CCCCGGCTGC CCCCGGCGCC GCCGCGGGGC

CTGCGCTCAG CCCGGTGCCA CCTGTG

TCCCAGCCCG GGCACACGCC CCATMCAGCC GCATCCCGSG ACCCGGTCGC            (SEQ ID NO:37)

CAGGACCTCG CCGCTGCAGA CCCCGGCTGC CCCCGGCGCC GCCGCGGGGC

CTGCGCTCAG CCCGGTGCCA CCTGTGGT
```

```
TCCCAGCCCG GGCACACGCC CCATMCAGCC GCATCCCGSG ACCCGGTCGC           (SEQ ID NO:38)
CAGGACCTCG CCGCTGCAGA CCCCGGCTGC CCCCGGCGCC GCCGCGGGGC
CTGCGCTCAG CCCGGTGCCA CCTGTGGTC
TCCCAGCCCG GGCACACGCC CCATMCAGCC GCATCCCGSG ACCCGGTCGC           (SEQ ID NO:39)
CAGGACCTCG CCGCTGCAGA CCCCGGCTGC CCCCGGCGCC GCCGCGGGGC
CTGCGCTCAG CCCGGTGCCA CCTGTGGTCC
TCCCAGCCCG GGCACACGCC CCATMCAGCC GCATCCCGSG ACCCGGTCGC           (SEQ ID NO:40)
CAGGACCTCG CCGCTGCAGA CCCCGGCTGC CCCCGGCGCC GCCGCGGGGC
CTGCGCTCAG CCCGGTGCCA CCTGTGGTCC A
TCCCAGCCCG GGCACACGCC CCATMCAGCC GCATCCCGSG ACCCGGTCGC           (SEQ ID NO:41)
CAGGACCTCG CCGCTGCAGA CCCCGGCTGC CCCCGGCGCC GCCGCGGGGC
CTGCGCTCAG CCCGGTGCCA CCTGTGGTCC AC
TCCCAGCCCG GGCACACGCC CCATMCAGCC GCATCCCGSG ACCCGGTCGC           (SEQ ID NO:42)
CAGGACCTCG CCGCTGCAGA CCCCGGCTGC CCCCGGCGCC GCCGCGGGGC
CTGCGCTCAG CCCGGTGCCA CCTGTGGTCC ACC
TCCCAGCCCG GGCACACGCC CCATMCAGCC GCATCCCGSG ACCCGGTCGC           (SEQ ID NO:43)
CAGGACCTCG CCGCTGCAGA CCCCGGCTGC CCCCGGCGCC GCCGCGGGGC
CTGCGCTCAG CCCGGTGCCA CCTGTGGTCC ACCT
TCCCAGCCCG GGCACACGCC CCATMCAGCC GCATCCCGSG ACCCGGTCGC           (SEQ ID NO:44)
CAGGACCTCG CCGCTGCAGA CCCCGGCTGC CCCCGGCGCC GCCGCGGGGC
CTGCGCTCAG CCCGGTGCCA CCTGTGGTCC ACCTG
TCCCAGCCCG GGCACACGCC CCATMCAGCC GCATCCCGSG ACCCGGTCGC           (SEQ ID NO:45)
CAGGACCTCG CCGCTGCAGA CCCCGGCTGC CCCCGGCGCC GCCGCGGGGC
CTGCGCTCAG CCCGGTGCCA CCTGTGGTCC ACCTGR
TCCCAGCCCG GGCACACGCC CCATMCAGCC GCATCCCGSG ACCCGGTCGC           (SEQ ID NO:46)
CAGGACCTCG CCGCTGCAGA CCCCGGCTGC CCCCGGCGCC GCCGCGGGGC
CTGCGCTCAG CCCGGTGCCA CCTGTGGTCC ACCTGRC
TCCCAGCCCG GGCACACGCC CCATMCAGCC GCATCCCGSG ACCCGGTCGC           (SEQ ID NO:47)
CAGGACCTCG CCGCTGCAGA CCCCGGCTGC CCCCGGCGCC GCCGCGGGGC
CTGCGCTCAG CCCGGTGCCA CCTGTGGTCC ACCTGRCC
TCCCAGCCCG GGCACACGCC CCATMCAGCC GCATCCCGSG ACCCGGTCGC           (SEQ ID NO:48)
CAGGACCTCG CCGCTGCAGA CCCCGGCTGC CCCCGGCGCC GCCGCGGGGC
CTGCGCTCAG CCCGGTGCCA CCTGTGGTCC ACCTGRCCC
TCCCAGCCCG GGCACACGCC CCATMCAGCC GCATCCCGSG ACCCGGTCGC           (SEQ ID NO:49)
CAGGACCTCG CCGCTGCAGA CCCCGGCTGC CCCCGGCGCC GCCGCGGGGC
CTGCGCTCAG CCCGGTGCCA CCTGTGGTCC ACCTGRCCCT
TCCCAGCCCG GGCACACGCC CCATMCAGCC GCATCCCGSG ACCCGGTCGC           (SEQ ID NO:50)
CAGGACCTCG CCGCTGCAGA CCCCGGCTGC CCCCGGCGCC GCCGCGGGGC
CTGCGCTCAG CCCGGTGCCA CCTGTGGTCC ACCTGRCCCT C
```

REFERENCES

1. Y. Tsujimoto et al., *Science*, 228: 1440–1443, 1985.
2. A. Bakhshi et al., *Cell*, 41: 899–906, 1985.
3. M. L. Cleary et al., *Cell*, 47: 19–28, 1986.
4. T. J. McDonnell et al., *Cancer Res.*, 52: 6940–6944, 1992.
5. F. Pezzella et al., *N. Engl. J. Med.*, 329: 690–694, 1994.
6. Q. L. Lu et al., *Internatl. J. Cancer*, 53: 29–35, 1993.
7. S. J. Korsmeyer, *Blood*, 80: 879–886, 1992.
8. J. C. Reed, *J. Cell. Biol.*, 124: 1–6, 1994.
9. C. J. Hawkins and D. L. Vaux, *Immunol. Reviews*, 142: 127–139, 1994.
10. G. T. Williams, *Cell*, 65: 1097–1098, 1991.
11. D. L. Vaux et al., *Nature*, 335: 440–442, 1988.
12. D. S. Askew et al., *Oncogene*, 6: 1915–1922, 1991.
13. G. 1. Evan et al., *Cell*, 69: 119–128, 1992.
14. A. J. Wagner et a., *Mol. Cell. Biol.*, 13: 2432–2440, 1993.
15. R. P. Bissonnette et al., *Nature*, 359: 552–554, 1992.
16. A. Fanidi et al., *Nature*, 359, 554–556, 1992.
17. J. J. Ryan et al., *Proc. Natl. Acad. Sci. U.S.A.*, 91: 5878–5882, 1994.
18. T. Miyashita et al., *Cancer Res.*, 54: 3131–3135, 1994.
19. M. Selvakumaran et al., *Oncogene*, 9: 1791–1798, 1994.
20. S. K. Chiou, et al., *Mol. Cell. Biol.*, 14: 2556–2563, 1994.
21. T. Subramanian, et al., *Oncogene*, 11: 2404–2409, 1995.
22. M. Seto et al., *EMBO*, 7: 123–131, 1988.
23. T. R. Fuerst et al., *Mol. Cell. Biol.*, 7: 2538–2544, 1987.
24. A. J. Wagner et al., *Genes Dev.*, 8: 2817–2830, 1994.
25. M. Oren, *Seminars Cancer Biol.*, 5: 221–227, 1994.
26. D. Michalovitz et al., *Cell*, 62: 671–680, 1990.
27. M. Debbas and E. White, *Genes Dev.*, 7: 546–554, 1993.
28. C. T. Chien et al., *Proc. Natl. Acad. Sci. USA*, 88: 9578–9582, 1991.
29. J. M. Boyd et al., *Cell*, 79: 341–351, 1994.
30. H-G. Wang et al., *Oncogene*, 9: 2751–2756, 1994.
31. T. Chittenden et al., *Nature*, 374: 733–736, 1995.
32. J. M. Boyd et al., *Oncogene*, 11: 1921–1928, 1995.
33. Z. N. Oltvai et al., *Cell*, 74: 609–619, 1993.
34. S. Haldar et al., *Proc. Natl. Acad. Sci. USA*, 92: 4507–4511, 1995.
35. S. Henderson et al., *Proc. Natl. Acad. Sci. USA*, 90: 8479–8483, 1993.
36. B. Tarodi et al., *Virology*, 201: 404–407, 1994.
37. S. Takayama et al., *DNA and Cell Biol.*, 13: 679–692, 1994.
38. T. Sato et a., *Proc. Natl. Acad. Sci. USA*, 91: 9238–9242, 1994.
39. S. Fields and O. K. Song, *Nature*, 340: 245–246, 1989.
40. J. A. Pietenpol, *Cancer Research*, 54: 3714–3717, 1994.
41. M. Seto et al., *The EMBO Journal*, 7: 123–131, 1988.
42. Y. Tsujimoto et al., *Proc. Natl. Acad. Sci. U.S.A.*, 83: 5214–5218, 1986.
43. D. B. Smith et al., *Gene*, 67: 31–40, 1988.
44. Z. N. Oltvai et al., *Cell*, 74: 609–619, 1993.
45. S. Takayama et al., *Cell*, 80: 279–284, 1995.
46. C. -Y Chen and D. V. Faller, *Oncogene*, 11: 1487–1498, 1995.
47. C. -Y Chen and D. V. Faller, *J. Biol. Chem.*, 271: 2376–2379, 1996.
48. S. Haldar et al., *Proc. Natl. Acad. Sci. U.S.A.*, 92: 4507–4511, 1995.
49. W. S. May et al., *J. Biol. Chem.*, 269: 26865–26870, 1994.
50. S. Tanaka et al., *Blood*, 79: 229–237, 1992.
51. M. L. Cleary et al., *Cell*, 47: 19–28, 1986.
52. M. J. Fernanadez-Sarabia and J. R. Bischoff, *Nature*, 366: 274–275, 1993.
53. E. Y. Skolnik et al., *Cell*, 65: 83–90, 1991.
54. W. G. Kaelin et al., Cell, 70: 351–364, 1992.
55. M. Orita et al., *Genomics*, 5: 874–879, 1989.
56. M. Orita et al., *Proc. Natl. Acad. Sci. U.S.A.*, 86: 2766–2770, 1989.
57. A. J. Montandon et al., *Nucleic Acids Res.*, 17: 3347, 1989.

What is claimed:

1. An isolated antibody that specifically binds to the AP domain of Bcl-2 or a fragment thereof, wherein said AP domain or fragment thereof is a Bcl-2 protein comprising residues 51 to any of 85–97 (SEQ ID NOS: 1–13) or a fragment thereof that contains at least one of Ser residue 51, Pro residue 57, Ser residue 62, Thr and Ser residues 69 and 70, Thr residue 74, and Pro residue 75, wherein said fragment exhibits full or partial anti-proliferation activity of the AP domain.

2. The isolated antibody of claim 1, wherein the AP domain consists of Bcl-2 residues 51 to 85 (SEQ ID NO: 1).

3. The isolated antibody of claim 1, wherein the antibody is a monoclonal antibody that specifically binds to the AP domain.

4. The isolated antibody of claim 2, wherein the antibody is a monoclonal antibody that specifically binds to the AP domain.

5. A hybridoma that makes the monoclonal antibody of claim 3.

6. A hybridoma that makes the monoclonal antibody of claim 4.

* * * * *

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala
        35
```

(2) INFORMATION FOR SEQ ID NO:2:

(i) SEQUENCE CHARACTERISTICS:
    (A) LENGTH: 36 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:2:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu
        35
```

(2) INFORMATION FOR SEQ ID NO:3:

(i) SEQUENCE CHARACTERISTICS:
        (A) LENGTH: 37 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser
        35
```

(2) INFORMATION FOR SEQ ID NO:4:

(i) SEQUENCE CHARACTERISTICS:
        (A) LENGTH: 38 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro
        35
```

(2) INFORMATION FOR SEQ ID NO:5:

(i) SEQUENCE CHARACTERISTICS:
        (A) LENGTH: 39 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Ser Gln Pro Gly His Thr Pro His Xaa Ala Ala Ser Arg Asp Pro Val
1               5                   10                  15
```

```
Ala Arg Thr Ser Pro Leu Gln Thr Pro Ala Ala Pro Gly Ala Ala Ala
            20                  25                  30

Gly Pro Ala Leu Ser Pro Val
        35
```

(2) INFORMATION FOR SEQ ID NO:6:

(i) SEQUENCE CHARACTERISTICS:
        (A) LENGTH: 40 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro
        35                  40
```

(2) INFORMATION FOR SEQ ID NO:7:

(i) SEQUENCE CHARACTERISTICS:
        (A) LENGTH: 41 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro
        35                  40
```

(2) INFORMATION FOR SEQ ID NO:8:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro Val
        35                  40
```

(2) INFORMATION FOR SEQ ID NO:9:

(i) SEQUENCE CHARACTERISTICS:
        (A) LENGTH: 43 amino acids
        (B) TYPE: amino acid

```
        (C) STRANDEDNESS:
        (D) TOPOLOGY: linear (ii) MOLECULE TYPE: protein (xi) SEQUENCE DESCRIPTION: SEQ ID NO:9:

Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro Val Val
        35                  40

(2) INFORMATION FOR SEQ ID NO:10:

(i) SEQUENCE CHARACTERISTICS:
        (A) LENGTH: 44 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro Val Val His
        35                  40

(2) INFORMATION FOR SEQ ID NO:11:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro Val Val His Leu
        35                  40              45

(2) INFORMATION FOR SEQ ID NO:12:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30
```

```
Gly Pro Ala Leu Ser Pro Val Pro Pro Val Val His Leu Xaa
        35                  40                  45
```

(2) INFORMATION FOR SEQ ID NO:13:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

```
Ser Gln Pro Gly His Thr Pro His Xaa Ala Ala Ser Arg Asp Pro Val
1               5                   10                  15

Ala Arg Thr Ser Pro Leu Gln Thr Pro Ala Ala Pro Gly Ala Ala Ala
            20                  25                  30

Gly Pro Ala Leu Ser Pro Val Pro Pro Val Val His Leu Xaa Leu
        35                  40                  45
```

(2) INFORMATION FOR SEQ ID NO:14:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGC                     104
```

(2) INFORMATION FOR SEQ ID NO:15:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCG                    105
```

(2) INFORMATION FOR SEQ ID NO:16:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGC                   106
```

(2) INFORMATION FOR SEQ ID NO:17:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCT                  107

(2) INFORMATION FOR SEQ ID NO:18:

(i) SEQUENCE CHARACTERISTICS:
        (A) LENGTH: 108 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTC                 108

(2) INFORMATION FOR SEQ ID NO:19:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCA                109

(2) INFORMATION FOR SEQ ID NO:20:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG               110

(2) INFORMATION FOR SEQ ID NO:21:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG C          111

(2) INFORMATION FOR SEQ ID NO:22:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CC         112

(2) INFORMATION FOR SEQ ID NO:23:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCC        113

(2) INFORMATION FOR SEQ ID NO:24:

(i) SEQUENCE CHARACTERISTICS:
        (A) LENGTH: 114 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCG       114

(2) INFORMATION FOR SEQ ID NO:25:

(i) SEQUENCE CHARACTERISTICS:
        (A) LENGTH: 115 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCGG      115

(2) INFORMATION FOR SEQ ID NO:26:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGT     116

(2) INFORMATION FOR SEQ ID NO:27:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTG     117

(2) INFORMATION FOR SEQ ID NO:28:

(i) SEQUENCE CHARACTERISTICS:
        (A) LENGTH: 118 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGC     118

(2) INFORMATION FOR SEQ ID NO:29:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCC     119

(2) INFORMATION FOR SEQ ID NO:30:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

(2) INFORMATION FOR SEQ ID NO:31:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

C                                                                   121

(2) INFORMATION FOR SEQ ID NO:32:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CC                                                                  122

(2) INFORMATION FOR SEQ ID NO:33:

(i) SEQUENCE CHARACTERISTICS:
        (A) LENGTH: 123 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CCT                                                                 123

(2) INFORMATION FOR SEQ ID NO:34:

(i) SEQUENCE CHARACTERISTICS:
        (A) LENGTH: 124 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TCCCAGCCCG GGCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CCTG                                                                124

(2) INFORMATION FOR SEQ ID NO:35:

(i) SEQUENCE CHARACTERISTICS:
        (A) LENGTH: 125 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

TCCCAGCCCG GGCACACGCC CCATMCAGCC GCATCCCGSG ACCCGGTCGC CAGGACCTCG    60

CCGCTGCAGA CCCCGGCTGC CCCCGGCGCC GCCGCGGGGC CTGCGCTCAG CCCGGTGCCA   120

CCTGT                                                              125

(2) INFORMATION FOR SEQ ID NO:36:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TCCCAGCCCG GGCACACGCC CCATMCAGCC GCATCCCGSG ACCCGGTCGC CAGGACCTCG    60

CCGCTGCAGA CCCCGGCTGC CCCCGGCGCC GCCGCGGGGC CTGCGCTCAG CCCGGTGCCA   120

CCTGTG                                                             126

(2) INFORMATION FOR SEQ ID NO:37:

(i) SEQUENCE CHARACTERISTICS:
        (A) LENGTH: 128 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

TCCCAGCCCG GGCACACGCC CCATMCAGCC GCATCCCGSG ACCCGGTCGC CAGGACCTCG    60

CCGCTGCAGA CCCCGGCTGC CCCCGGCGCC GCCGCGGGGC CTGCGCTCAG CCCGGTGCCA   120

CCTGTGGT                                                           128

(2) INFORMATION FOR SEQ ID NO:38:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

TCCCAGCCCG GGCACACGCC CCATMCAGCC GCATCCCGSG ACCCGGTCGC CAGGACCTCG    60

CCGCTGCAGA CCCCGGCTGC CCCCGGCGCC GCCGCGGGGC CTGCGCTCAG CCCGGTGCCA   120

CCTGTGGTC                                                          129

(2) INFORMATION FOR SEQ ID NO:39:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

| TCCCAGCCCG GGCACACGCC CCATMCAGCC GCATCCCGSG ACCCGGTCGC CAGGACCTCG | 60 |
| CCGCTGCAGA CCCCGGCTGC CCCCGGCGCC GCCGCGGGGC CTGCGCTCAG CCCGGTGCCA | 120 |
| CCTGTGGTCC | 130 |

(2) INFORMATION FOR SEQ ID NO:40:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

| TCCCAGCCCG GGCACACGCC CCATMCAGCC GCATCCCGSG ACCCGGTCGC CAGGACCTCG | 60 |
| CCGCTGCAGA CCCCGGCTGC CCCCGGCGCC GCCGCGGGGC CTGCGCTCAG CCCGGTGCCA | 120 |
| CCTGTGGTCC A | 131 |

(2) INFORMATION FOR SEQ ID NO:41:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

| TCCCAGCCCG GGCACACGCC CCATMCAGCC GCATCCCGSG ACCCGGTCGC CAGGACCTCG | 60 |
| CCGCTGCAGA CCCCGGCTGC CCCCGGCGCC GCCGCGGGGC CTGCGCTCAG CCCGGTGCCA | 120 |
| CCTGTGGTCC AC | 132 |

(2) INFORMATION FOR SEQ ID NO:42:

(i) SEQUENCE CHARACTERISTICS:
        (A) LENGTH: 133 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

| TCCCAGCCCG GGCACACGCC CCATMCAGCC GCATCCCGSG ACCCGGTCGC CAGGACCTCG | 60 |
| CCGCTGCAGA CCCCGGCTGC CCCCGGCGCC GCCGCGGGGC CTGCGCTCAG CCCGGTGCCA | 120 |
| CCTGTGGTCC ACC | 133 |

(2) INFORMATION FOR SEQ ID NO:43:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:43:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCGGTGCCA     120

CCTGTGGTCC ACCT                                                       134
```

(2) INFORMATION FOR SEQ ID NO:44:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:44:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCGGTGCCA     120

CCTGTGGTCC ACCTG                                                      135
```

(2) INFORMATION FOR SEQ ID NO:45:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:45:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCGGTGCCA     120

CCTGTGGTCC ACCTGR                                                     136
```

(2) INFORMATION FOR SEQ ID NO:46:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:46:

```
TCCCAGCCCG GGCACACGCC CCATMCAGCC GCATCCCGSG ACCCGGTCGC CAGGACCTCG      60

CCGCTGCAGA CCCCGGCTGC CCCCGGCGCC GCCGCGGGGC CTGCGCTCAG CCCGGTGCCA     120

CCTGTGGTCC ACCTGRC                                                    137
```

(2) INFORMATION FOR SEQ ID NO:47:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:47:

```
TCCCAGCCCG GGCACACGCC CCATMCAGCC GCATCCCGSG ACCCGGTCGC CAGGACCTCG      60
```

```
CCGCTGCAGA CCCCGGCTGC CCCCGGCGCC GCCGCGGGGC CTGCGCTCAG CCCGGTGCCA    120

CCTGTGGTCC ACCTGRCC                                                  138
```

(2) INFORMATION FOR SEQ ID NO:48:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:48:

```
TCCCAGCCCG GCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CCTGTGGTCC ACCTGRCCC                                                 139
```

(2) INFORMATION FOR SEQ ID NO:49:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:49:

```
TCCCAGCCCG GCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CCTGTGGTCC ACCTGRCCCT                                                140
```

(2) INFORMATION FOR SEQ ID NO:50:

(i) SEQUENCE CHARACTERISTICS:
        (A) LENGTH: 141 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:50:

```
TCCCAGCCCG GCACACGCC CCATMCAGCC GCATCCCGSG ACCCGGTCGC CAGGACCTCG     60

CCGCTGCAGA CCCCGGCTGC CCCCGGCGCC GCCGCGGGGC CTGCGCTCAG CCCGGTGCCA    120

CCTGTGGTCC ACCTGRCCCT C                                              141
```

(2) INFORMATION FOR SEQ ID NO:51:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer"

(xi) SEQUENCE DESCRIPTION: SEQ ID NO:51:

```
GGACCACAGG TGGCACCGGG CTGAGGCTAG CGGAGAAGAA GCCCGGTGCG GGGGCG        56
```